United States Patent [19]

Martin

[11] Patent Number: 5,252,606
[45] Date of Patent: Oct. 12, 1993

US005252606A

[54] FORTIFIED GLUTARALDEHYDE DISINFECTANT

[76] Inventor: Howard Martin, 909 Pershing Dr., Silver Spring, Md. 20910

[21] Appl. No.: 468,186

[22] Filed: Jan. 22, 1990

[51] Int. Cl.$^5$ .................... A61K 31/19; A61K 31/14; A61K 31/11; A61K 31/05
[52] U.S. Cl. .................... 514/574; 514/643; 514/698; 514/705; 514/731
[58] Field of Search ............... 514/643, 642, 574, 698, 514/705, 724, 731

[56] References Cited

U.S. PATENT DOCUMENTS 4,764,527  8/1988  Wagner et al. .................... 514/256
4,923,899  5/1990  Wachman et al. .................. 514/642

OTHER PUBLICATIONS

Chem Abst, 101: 177581v (1984) Martin.

*Primary Examiner*—Zohreh A. Fay

[57] ABSTRACT

A highly fortified glutaraldehyde formulation is provided consisting of guaternary ammonium chloride; glutaraldehyde; para tertiary amylphenol; citric acid, isopropyl alcohol, and water to form a concentrated formulation which may be diluted as requested.

1 Claim, No Drawings

FORTIFIED GLUTARALDEHYDE DISINFECTANT

BACKGROUND AND SUMMARY OF THE INVENTION

This invention is an improvement over the chemical disinfectant and sterilant composition disclosed in my U.S. Pat. No. 4,469,614 and U.S. Pat. No. 4,654,374.

| Prior Art Patents | | | |
|---|---|---|---|
| 3,915,877 | 10/1975 | Ware | 252/106 |
| 4,208,404 | 06/1980 | Cowan | 424/153 |
| 4,469,614 | 09/1984 | Martin | 514/705 |
| 4,654,374 | 05/1987 | Martin | 514/698 |

A new and unique combination of various independent biocides has been formulated. Glutaraldehyde in the acidic form has been shown by several investigators, including this inventor, to be superior to the alkaline form of glutaraldehyde in cidal effectiveness.

However, the product has been shown to be erratic in killing effectiveness against mycobacterium tuberculosis, as a sporicide for sterilization, and especially in effectiveness against the polio virus.

The rate of reaction is pH dependent. Acidic glutaraldehyde is more stable than alkaline forms. Solutions above pH 8, which are activated, lose effectiveness within four (4) weeks while those solutions below neutral can remain active for up to two (2) years. Organic matter does not rapidly diminish the effect of acidic glutaraldehyde in contrast to alkaline glutaraldehyde.

The two phenolics chosen for this combination product are para tertiary amylphenol and ortho phenylphenol. The para substitution increases antibacterial activity by increasing surface action. However, it also decreases water solubility. The ortho form increases antibacterial action.

The difficulty in the past has been to maintain these phenolics in an aqueous solution. The new formulation of this invention maintains the phenolics in a solubilized system that has not previously been available.

The ability to maintain the phenolics in acidic solution potentiates their antimicrobial activity. The low pH of this new formulation enables a lower concentration of phenolics to accomplish the equivalent killing effectiveness of higher concentrations used in previous formulations. Phenolics will sometimes be affected by reacting with organic matter. Ortho phenylphenol is effective against TB, while glutaraldehyde is slow and the quaternary ammonium chloride is only inhibitory.

Quaternary ammonium chloride (QAC) is a cationic surface acting agent. QAC is effective as it penetrates the lipid coating of TB. However, it has been shown in the 1970's to be inactivated by hard water; it is merely inhibitory when used alone.

The QAC's are primarily active against gram positive organisms and require very high concentrations against gram negative organisms. QAC's are not effective against mycobacterium tuberculosis. Viruses are more resistant than bacteria and fungi to the QAC's which have poor effects against hydrophilic types (enteroviruses, polio, coxsackie and ECHO).

In addition, QAC's are fungistatic rather than fungicidal. They are greatly affected by organic matter. Depending upon its concentration, phenol will retard or inhibit germination of bacterial spores, as will acidic glutaraldehyde. However, QAC's allow germination to proceed but inhibit outgrowth. QAC's act on the bacterial cell membrane in a manner similar to hemolysis while phenols promote a concentration-dependent leakage of cell contents from microbial cells.

Alcohols have been shown to have antimicrobial properties. They are fast acting but are poor against spores and viruses. Usually the most effective concentration of the superior alcohols (ethyl alcohol and isopropyl alcohol) is about 60-70%. Ethyl alcohol is popular because of lack of odor and low irritation. Isopropyl alcohol is considered to be more effective against bacteria than ethyl alcohol.

Alcohol is effective against mycobacterium tuberculosis. The isopropyl alcohol bactericidal effectiveness paralleled that of ethyl alcohol but surpassed ethyl alcohol in lower ranges. Either isopropyl or ethyl alcohol may be utilized within the formulation.

The combination of chemicals of the present invention create a synergistic effect that leads to a superior combination. Each part adds a different aspect to cidal effectiveness as well as enhances and creates a superior and more effective chemical sterilant/disinfectant than is achievable by the individual components.

The particular proportions of the components are important so as to maintain their solubility and ideal effectiveness at the lowest concentrations. The low pH maintained by the citric acid is another unusual and key feature of the invention. On its own, this combination is bactericidal and its spectrum of activity includes all the common non sporing pathogens including tubercle bacilli. The ethanol or isopropyl alcohol acts as a solvent to release constituents which leads to bacterial death. It is also virucidal against both hydrophilic and lipophilic viruses.

With this unique combination of ingredients, the ability of the organic matter and the minerals in the water to reduce cidal effectiveness of the gluteraldehyed and QAC is diminished. In addition, the toxic side-effects of the solution are minimized due to the synergism which effect allows a lower concentration to be used while maintaining effectiveness. QAC is effective now in lower concentrations than it would be if utilized alone.

This new biocide formulation is quick acting (less down time to disinfect), has a broad spectrum of biocidal activity, has a detergent property necessary for proper cleansing and penetration, is not corrosive, at use dilution has good skin tolerance, and is easily disposable. The alcohol is held in solution in this formulation by the QAC's while the gluaraldehyde exerts its bactericidal effect and the phenolics exert their tuberculocidal effects which enhancing the glutaraladehyde and QAC effects.

This new combination of chemicals allows each part to enhance the other for a superior effect. In laboratory testing, this new combination formulation lead to unexpected results that indicate a superior cidal effectiveness at much reduced concentrations, approximately one-half of that of previous combinations.

In field service testing, it was demonstrated that the new formulation was able to penetrate, clean and disinfect an industrial oil well head in one treatment using this single product alone. This is normally accomplished by multiple products.

These unusual results indicate the uniqueness of the formulation: its ability to coalesce and maintain these independent compounds in one solubilized, stable, aqueous solution, this enabled the new superior biocidal compound to be developed.

One of the objects of this invention is to provide a fortified glutaraldehyde compound having unique characteristics.

Another object of this invention is to provide a high fortified glutaraldehyde formulation that can be used effectively and efficiently in industrial, commercial, and agricultural areas to kill sulfate reducing bacteria that are specific to corrosion problems in the oil producing area.

Still another object of this invention is to provide a high fortified glutaraldehyde that can be used in industrial situations requiring cleaning and disinfecting at higher concentrations.

A further object of this invention is to provide a new highly fortified glutaraldehyde formulation that has a broad spectrum of biocidal activity.

A further object is to provide a fortified glutaraldehyde formulation that has a detergent property necessary for proper cleansing and penetration is still another object of this invention.

An additional object is to provide a high fortified glutaraldehyde formulation which, when in use, is not corrosive and which has good skin tolerance and is easily disposable, are other objects of this invention.

To provide a high fortified glutaraldehyde formulation in which the chemicals thereof allow each part to enhance the other for superior effects is still another object of this invention.

This new formulation consists of the following parts by weight and/or percent:

|  | Weight | Percent |
| --- | --- | --- |
| Dual quaternary ammonium chloride (N-alkyldimethylethylbenzyl ammonium chloride) (N-alkyldimethyl benzyl ammonium chloride) | 12.50 grams | 12.50% |
| Glutaraldehyde | 25.00 grams | 25.00% |
| Para tertiary amylphenol | 1.00 gram | 1.00% |
| Ortho phenylphenol | 1.00 gram | 1.00% |
| Citric acid | 0.25 grams | .25% |
| Isopropyl alcohol | 14.00 grams | 14.00% |
| Water | 46.25 grams | 46.25% |
| TOTAL | 100.00 grams | 100.00% |

The formulation has usage in the health field and industrial, agricultural and consumer area. The formulation may be in the form of an immersion solution, a spray, or a wipe. It may be activated by ultrasound, thermal activity, microwaves, radiation, ultraviolet, or any other energy source for enhancement of effect. The formulation listed above is the concentrated form. The formulation may be diluted for use.

As can be readily understood from the foregoing description of a high fortified glutaraldehyde formulation, the present structured formation can be further structured in different modes of formulation to provide an ability to disinfect and sterilize articles, surfaces, and the like.

Accordingly, modifications and variations to which the formulation is susceptible may be practiced without departing from the scope and intent of the appended claims.

What is claimed is;

1. A high fortified glutaraldehyde, comprising, a basic formulation of chemical ingredients, said formulation of chemical ingredients consisting of the following optimal quantities of formation of chemical ingredients, said formulation of said chemical ingredients being used to form a base stock solution, said optimal quantities being by weight of the total weight of said basic formulation of chemical ingredients: dual quaternary ammonium chloride 12.5 grams, glutaraldehyde 25.0 grams, para tertiary amylphenol 1.0 gram, citric acid 0.25 grams, isopropyl alcohol 14.0 grams, and water 46.25 grams, wherein said formulation of chemical ingredients includes glutaraldehyde which has an initial concentration between 25.0 grams glutaraldehyde and 0.05 grams glutaraldehyde per 100 grams solution.

* * * * *